United States Patent [19]

McCarthy et al.

[11] 3,993,064
[45] Nov. 23, 1976

[54] ONE-HANDED SYRINGE

[75] Inventors: Charles J. McCarthy, Rockville; Steven Charles; Daniel M. Eichenbaum, both of Bethesda, all of Md.

[73] Assignee: The United States of America as represented by the Department of Health, Education and Welfare, Washington, D.C.

[22] Filed: Mar. 27, 1975

[21] Appl. No.: 563,378

[52] U.S. Cl..................... 128/218 A; 128/218 PA; 128/236
[51] Int. Cl.²......................................... A61M 5/00
[58] Field of Search........ 128/218 R, 218 A, 218 C, 128/218 P, 218 PA, 214, 236, 215, 216, 224, 234; 222/390, 43; 141/26, 375, 329, 330, 27; 92/136

[56] References Cited
UNITED STATES PATENTS

| 2,498,672 | 2/1950 | Glass | 128/218 A |
| 2,622,765 | 12/1952 | Gilmont | 128/236 X |
| 2,771,217 | 11/1956 | Brown et al. | 222/390 X |
| 3,279,653 | 10/1966 | Pfleger | 128/218 A |
| 3,833,030 | 9/1974 | Waldbauer, Jr. et al. | 141/375 X |
| 3,841,331 | 10/1974 | Wilder et al. | 128/218 A |

FOREIGN PATENTS OR APPLICATIONS

| 819,629 | 10/1937 | France | 128/236 |
| 800,588 | 10/1950 | Germany | 128/218 C |
| 1,179,888 | 2/1970 | United Kingdom | 128/218 C |

*Primary Examiner*—John D. Yasko
*Attorney, Agent, or Firm*—Browdy and Neimark

[57] ABSTRACT

A one-handed, self-contained, light-weight syringe for use in applying suction during a surgical operation includes a standardized syringe mounted into a longitudinally cut tube with a wheel attached at a right angle to the tube axis. The surgeon-operator, by turning this wheel with his fingers, may operate the syringe and control the amount of suction. The wheel is fastened to a pinion gear which rotates on a fixed shaft causing a rack and syringe plunger to move relative to the syringe barrel. This device allows the syringe barrel to move very smoothly and also enables the surgeon-operator complete freedom of one hand.

7 Claims, 5 Drawing Figures

ONE-HANDED SYRINGE

FIELD OF THE INVENTION

This invention relates to a one-handed syringe which can be used in situations where suction is desired at a body orifice or tissue in surgical operations, and which has particular utility in the aspiration of the vitreous humor of the human eye.

BACKGROUND OF THE INVENTION

Current methods of trans pars plana vitrectomy utilize suction force to imbricate the vitreous to be cut into the port of the vitrectomy machine. The surgical assistant provides a suction by manipulating a five to fifty cc plastic syringe while observing the surgeon's operative field through a stereo observation tube on the operating microscope. Advantages of this method are its inherent simplicity and the possibility of rapid reversal of the suction to disengage tissue from the cutting opening.

The prior art syringes which have been utilized in this method must be held by the surgical assistant with both hands to control the amount of suction. Due to friction in the syringe and the fatiguing effect to the assistant's fingers, the feel of suction level is greatly impaired causing imprecise response in time and pressure. To overcome this lack of precision and this difficulty of operation, a device which can be operated more precisely and more easily and with only one hand is necessary.

U.S. Pat. No. 2,771,217, issued to Brown et al. shows a measuring and dispensing device which may be operated only by one hand. While this device frees one of the operator's hands, it does not provide the sensitivity necessary to determine the amount of suction or pressure that is necessary. This is due in part to the use of a bushing seal, a threaded bore and detents so as to obstruct the sense of feel of the operator. Additionally, Brown's device was never meant to operate as the conventional, disposable syringe since it has no means to hold such a syringe and therefore could not even be applied to the vitreous operation previously described.

SUMMARY OF THE INVENTION

The present invention relates to a one-handed syringe which may be used to apply suction to a body orifice or tissue, and has particular utility in applying suction and sometimes pressure at the aspiration port of a vitrectomy machine during surgical operation on the human eye. This device applies the suction at the desired surface with increased controlled sensitivity without operative fatigue and without sacrificing the benefits of a lightweight, hand-held syringe.

The syringe itself consists basically of a longitudinally cut tube half with a wheel attached at a right angle to the tube axis. A standard type syringe fits inside the tube so that holding the tube in one hand is little more than holding the syringe by itself. Thus, the device is a self-contained, lightweight device. The control wheel is oriented so that the fingers of the same hand holding the tube can easily rotate the wheel in either direction with a smooth easy motion, thus overcoming the prior art disadvantage of having to use both hands.

Rotating the wheel turns a pinion gear on a rack which incorporates enough mechanical advantage to permit cavitation level of suctions with fingertip control of the wheel. The wheel is large as compared to the pinion but can easily be manipulated by the fingers or finger tips of the same hand which holds the syringe. This greatly improves the precision over the prior art by enabling the syringe barrel to be moved very smoothly. If the wheel is rotated in such a manner to move the plunger towards the forward end of the syringe, then pressure is applied to the area in contact with the tip of the syringe. Conversely, if the plunger is moving away from the forward end of the syringe, suction is applied to that area. In this manner, the syringe exhibits an infinitely variable rate of plunger motion.

The syringe barrel snaps into the tube half and a thumb screw fixes the end of the syringe plunger to the end of the gear rack. The pinion gear, which is fastened to the wheel, rotates on a fixed shaft causing the rack and plunger to move relative to the tube and syringe barrel.

It is, accordingly an object of the present invention to overcome the defects of the prior art, such as are indicated above.

Another object of the present invention is to provide a device which can apply both pressure or suction to a body tissue.

Another object of the present invention is to provide a syringe which can be used during a surgical operation on the human eye.

Still another object of the present invention is to provide a syringe which can be operated using only one hand.

Still a further object of the present invention is to provide a syringe which relieves excessive strain on the fingers of the operator.

Yet another object of the present invention is to provide a syringe which has improved control and precision.

Another object of the present invention is to provide a syringe which improves the response time for changing or reversing pressures.

One other object of the present invention is to provide a syringe which can be sterilized by autocalving.

Still another object of the present invention is to provide a syringe which exhibits an infinitely variable rate of plunger motion.

BRIEF DESCRIPTION OF THE DRAWING

The above and additional objects and advantages inherent in the present invention will become more apparent by reference to the description of an illustrated embodiment and a drawing thereof in which.

DETAILED DESCRIPTION OF A PREFERRED EMBODIMENT

Figure 1:
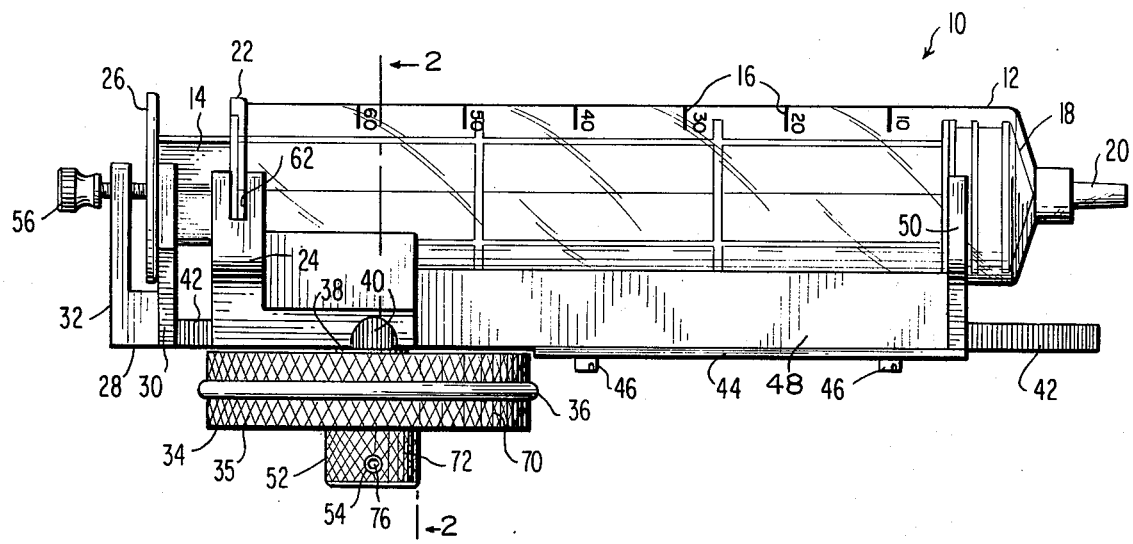
FIG. 1 is a side view of an embodiment of a syringe in accordance with the present invention.
Figure 2:
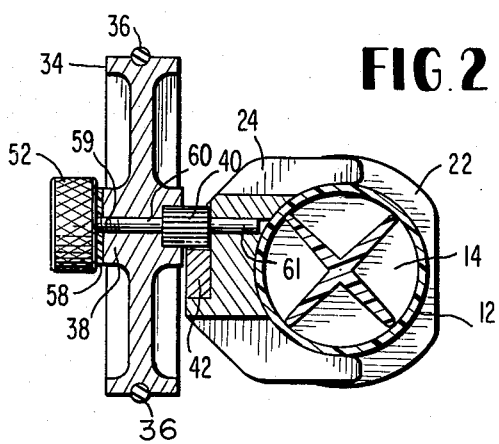
FIG. 2 is a sectional view taken along line 2—2 of FIG. 1 with the plunger in its fully retracted position.
Figure 4:
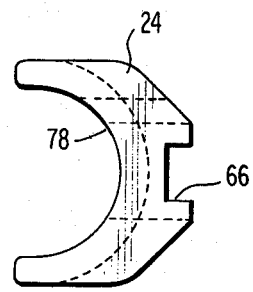
FIG. 4 is a side view of the barrel clamp of the device of FIG. 1.
Figure 3:
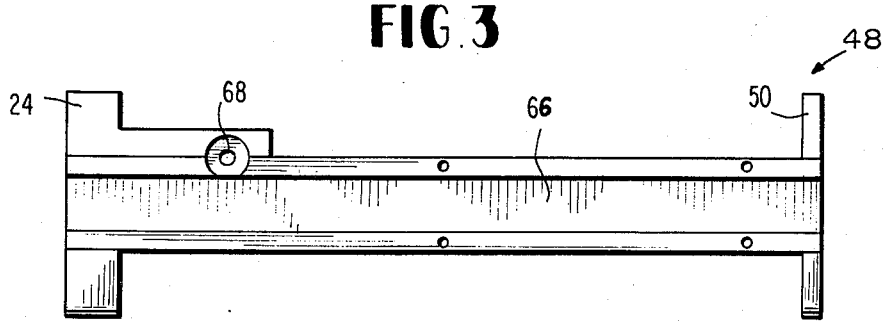
FIG. 3 is a top view of a longitudinally cut tube half in the device of FIG. 1.
Figure 5:
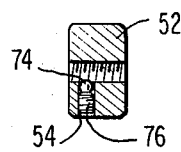
FIG. 5 is a view of the knurled nut of the device of FIG. 1.

FIGS. 1 and 2 show a preferred embodiment of a one-handed syringe 10. The basic components of the device 10 are a syringe barrel 12, syringe plunger 14, a longitudinally cut tube half 48 and a control wheel 34. While the size of the entire device can vary widely, the optimum size has been found to be between 6 and 8 inches in length.

The barrel 12 can be a standardized disposable cylindrical syringe barrel having a barrel tip 20 constituted of plastic or any like substance; such barrel 12 is snapped into the longitudinally cut tube half 48 which constitutes the body of the device 10. The barrel 12 is embossed with calibrations 16 to give the operator an indication of how much fluid is in the device. The barrel is anchored in place by two barrel clamps 24 and 50 which are disposed respectively at the ends of the tube 48. These clamps have a substantially semicircular configuration of the barrel. The barrel clamp 24 is disposed at the end furthest from the syringe barrel tip 20 and contains a semi-circular slot 62 which is adapted to receive a barrel flange 22.

A center bore 78 of the tube half 48 is designed to receive the main body of the syringe barrel 12, with the barrel clamp 50 adapted so that the end of the barrel will rest in its proper position. The tube half 48, less than half of a full tube, is used as the supporting body of the device 10 rather than a full tube in order to make the device lighter and therefore more easy to operate.

A groove 66 is cut into the external wall of the tube 48 so as to receive a rack 42, the function of which will be described in more detail subsequently, which slides longitudinally in the groove. A hole 68 is provided in the tube so that a shaft 60 (see FIG. 2) can be driven into the hole 68 to form a permanent attachment between the wheel 34, a pinion 40 and the tube 48. The tube half 48 can be constructed of any suitable material such as an anodized aluminum alloy, magnesium, titanium, stainless steel or a heat resistant light weight yet strong plastic such as Lexan. In this manner, the entire device may be sterilized by autoclaving.

The substantially cylindrical plunger 14, having a conical nose 18, is made of any suitable plastic type material, and is movably disposed within the syringe barrel 12. A plunger clamp 28 containing two clamp arms 30 and 32 is provided to connect one end of the rack 42 to a flange 26 at the end of the syringe plunger 14. This clamp 28 can be constructed of material similar to that of the tube 48. A knurled thumb screw 56 is provided to abut the plunger flange 26 so that the flange itself remains in its proper position. This screw 56 passes through a threaded hole which is bored into the clamp arm 32, and presses on the plunger flange 26, and constructed of the same material as the rack 42.

A cover 44 anchored by screws 46, and constructed of the same anodized aluminum composition as the clamp 28, is provided on the bottom of tube 48 so as to prevent the operator's glove from becoming caught in the rack 42 or pinion gear 40 during operation of the device.

Since the main purpose of the invention is to provide a syringe which may be operated with the use of only one hand, and which gives to the operator an increased control sensitivity so that he would know whether more suction or pressure is necessary, a highly efficient control and drive means for the plunger must be employed. A wheel 34 has been developed just for this purpose so that rotation of this wheel by the operator's fingertips allows the syringe plunger to move in and out of the syringe barrel. The control wheel is attached at a right angle to the longitudinal axis of the tube 48 and is oriented so that the fingers of the same hand holding the syringe can easily rotate the wheel in either direction with a smooth easy motion. A wheel having a diameter of approximately two inches has been found to give good results, however any size wheel which has a diameter large enough so that the fingertips can rotate it with very little force may be employed. The wheel is provided with a rubber surgical tire 36 to help prevent wet surgical gloves from slipping on it and additionally, the side surface 35 of the wheel is provided with serrations 70 to also prevent slippage.

The control wheel 34 is welded, force-fitted or otherwise permanently attached to the pinion gear 40 so that when the wheel is rotated, the pinion gear is also turned. This unconventional attachment of a pinion gear directly to the wheel can be made stronger than the more conventional attachment of a gear to shaft because the shaft radius is smaller than the gear hub radius and will therefore not stand as much torque. When in place, the wheel assembly is constructed so that the pinion gear 40 mates with the rack 42. Therefore, by turning the control wheel 34, the pinion gear 40 is forced to rotate and causes the rack 42 to move parallel to the axes of the tube 48 and the syringe barrel 12. Since the gear rack 42 has one end connected to plunger clamp 28 and thus to the syringe plunger 14 through the clamp 28, the turning of the wheel 34 causes the syringe plunger 14 to move in and out of the syringe barrel 12.

The wheel sub-assembly is shown most clearly in FIG. 2, where the pinion gear 40 and the hub 38 of the control wheel 34 are both provided in a central bore so that the axle-like shaft 60 having a smooth end 61 and threaded end 59 may connect this sub-assembly to the tube 48. This is accomplished by press fitting the smooth end 61 of the shaft 60 into hole 68 in the tube half 48. This simplified means of attachment provides a maximum resistance to bending in a cantilever fashion. The center part of the shaft 60 projects through the pinion gear 40 and the control wheel 34 in such a manner as to allow the pinion-wheel sub-assembly to freely rotate on the shaft. The threaded end 59 of the shaft 60 allows engagement with a knurled nut 52 to retain the pinion-wheel sub-assembly in place. This arrangement is far simpler than one having the pinion affixed to a rotating shaft with the requirement of a bearing surface on each end of the shaft and the additional requirement of keeping the shaft from moving along its axis while allowing it to move in a rotating direction. Furthermore, since the wheel 34 and the pinion 40 are assembled as one piece which rotates on the fixed shaft 60, higher torques may be allowed without breaking any of the connections.

The knurled nut 52, similar to the control wheel 34, has serrations 72 on its outer surface and may be constructed of the same material as the tube half 48 and serves the dual purpose of retaining the pinion-wheel sub-assembly and applying an anti-rotating force through a washer 58, preferably of Teflon, to the pinion-wheel sub-assembly. The knurled nut 52 contains a threaded hole 54 through which a Teflon ball 74 is pushed against the threaded part 59 of shaft 60. Thus, the knurled nut 52 can be tightened down on the control wheel 34 to prevent "free wheeling" or to adjust the operating tension. Furthermore, this configuration is to ensure that the knurled nut will not work itself loose from the desired position set by the user of the device. The Teflon ball 74 is pushed by a set screw 76 which may be tightened as needed, and is usually resilient enough to maintain the desired force on the thread of the shaft 60, but additional resiliency may be provided between the Teflon ball and the set screw by inserting a silicone rubber spring between them.

The design of the one-handed syringe and the drive means which is employed to move the plunger in and out, gives the user greater sensitivity in determining whether more pressure or more suction is desired at the point of use. In operation, the syringe is held in one hand and the wheel 34 is rotated by the fingers of that hand. The user places the tip 20 of the barrel at the point where aspiration is desired. If for example, the syringe is to be used in an eye operation in conjunction with a vitrectomy machine while the operator is observing the surgeon's operative field through a stereo observation tube on the operating microscope, the operator can continually apply either pressure or suction as warranted. A clock-wise turn of the control wheel 34 of the syringe as described herein enables the rack 42 and therefore plunger clamp 28 and the plunger 14 to move away from the tip 20 of the barrel. This movement allows suction to be applied to the vitreous humor. If pressure is now desired to be provided at this point, the control wheel is rotated in a counterclockwise movement thus bringing the end of the plunger 18 closer to the tip 20 of the barrel by exerting pressure. A cone like configuration on the end of the plunger 18 is provided so that the pressure is applied more efficiently to the tip of the barrel 20.

While this device has been described with particular reference to its use during eye surgery, it should not be considered to be so limited and may be utilized in many different operations or situations. It will be obvious to those skilled in the art that various changes may be made without departing from the scope of the invention and that the invention is not to be considered limited to what is shown in the drawings and described in the specification. For example, the parts may be formed of suitable substitute materials in place of those mentioned above.

We claim:

1. A one-handed syringe free of mounting brackets for the application of suction and pressure to a patient while being held in one hand of an operator comprising:
   a cylindrical syringe barrel having first and second ends, and a longitudinal axis;
   a cylindrical syringe plunger, movably disposed within said syringe barrel for longitudinal movement along said longitudinal axis;
   a barrel supporting means for the retention and holding of said syringe barrel;
   a rotatable control wheel rotatable by fingers of the same hand which holds the syringe, having an axis of rotation and a hub, said control wheel being mounted on said barrel support means with said axis of rotation being between said first and second ends, and being substantially perpendicular to said longitudinal axis; and
   drive means operatively connected between said control wheel and said syringe plunger for changing the position of said syringe plunger in said syringe barrel in response to the movement of said rotatable control wheel in either direction and allowing an operator to sense force being applied, said drive means being mounted on said barrel support means and being a rack and pinion, said control wheel being connected to said pinion which meshes with said rack to drive said rack and thereby drive said syringe plunger;
   whereby suction or pressure can be applied by an operator by rotating the control wheel with fingers of the same hand which holds the syringe free of need for providing any opposed torque about the longitudinal axis of the syringe barrel while allowing the operator complete freedom of his other hand.

2. A one-handed syringe for the application of suction or pressure according to claim 1, wherein said rack is connected to said syringe plunger by a plunger clamp.

3. A one-handed syringe for the application of suction or pressure according to claim 1, wherein said pinion is coaxial with and immovably fastened to said control wheel.

4. A one-handed syringe for the application of suction or pressure according to claim 1, wherein the axis of said control wheel is attached at a right angle to the axis of said tube.

5. A one-handed syringe for the application of suction or pressure comprising:
   a cylindrical syringe barrel;
   a cylindrical syringe plunger, movably disposed within said syringe barrel;
   a barrel supporting means for the retention and holding of said syringe barrel;
   a rotatable control wheel having a hub and mounted on said barrel support means;
   drive means operatively connected between said control wheel and said syringe plunger for changing the position of said syringe plunger in said syringe barrel in response to the movement of said rotatable control wheel, said drive means being mounted on said barrel support means and including a rack and pinion, said control wheel serving to rotate said pinion which meshes with said rack to drive said rack and thereby drive said syringe plunger; and
   a cylindrical shaft having a smooth end and a threaded end said smooth end being fixedly secured to said barrel supporting means and said threaded end passing through the center of said pinion and into the hub of said control wheel.

6. A one-handed syringe for the application of suction or pressure according to claim 5, wherein said shaft extends through said control wheel, and further containing a knurled nut on the end of said shaft for the retention of said wheel and said pinion in a fixed position with respect to said barrel supporting means.

7. A one-handed syringe for the application of suction or pressure according to claim 6, wherein said knurled nut includes a set screw and ball, whereby said set screw pushes said ball against said threaded end of said shaft to maintain said knurled nut in position.

* * * * *